US010035771B2

(12) United States Patent
Wang et al.

(10) Patent No.: US 10,035,771 B2
(45) Date of Patent: Jul. 31, 2018

(54) MERCAPTONICOTINIC ACID COMPOUND AND PREPARATION METHOD AND USE THEREOF

(71) Applicants: INSTITUTE OF MICROBIOLOGY AND EPIDEMIOLOGY, ACADEMY OF MILITARY MEDICAL SCIENCES, PR CHINA, Beijing (CN); THE SECOND MILITARY MEDICAL UNIVERSITY, Shanghai (CN)

(72) Inventors: Hui Wang, Beijing (CN); Wannian Zhng, Shanghai (CN); Zhenyuan Miao, Shanghai (CN); Tao Li, Beijing (CN); Xiong Liu, Beijing (CN); Yuelin Wu, Beijing (CN); Sen Luo, Beijing (CN); Chunquan Sheng, Shanghai (CN); Xiaoxue Lu, Beijing (CN); Jianzhong Yao, Shanghai (CN)

(73) Assignee: INSTITUTE OF MICROBIOLOGY AND EPIDEMIOLOGY, ACADEMY OF MILITARY MEDICAL SCIENCES, PR CHINA, Beijing (CN)

( * ) Notice: Subject to any disclaimer, the term of this patent is extended or adjusted under 35 U.S.C. 154(b) by 0 days.

(21) Appl. No.: 14/892,219

(22) PCT Filed: May 19, 2014

(86) PCT No.: PCT/CN2014/077768
§ 371 (c)(1),
(2) Date: Nov. 19, 2015

(87) PCT Pub. No.: WO2014/187291
PCT Pub. Date: Nov. 27, 2014

(65) Prior Publication Data
US 2016/0083347 A1    Mar. 24, 2016

(30) Foreign Application Priority Data

May 20, 2013   (CN) .......................... 2013 1 0187415
May 20, 2013   (CN) .......................... 2013 1 0188043

(51) Int. Cl.
*C07D 213/80*    (2006.01)
*C07D 213/803*    (2006.01)

(52) U.S. Cl.
CPC ....... *C07D 213/80* (2013.01); *C07D 213/803* (2013.01)

(58) Field of Classification Search
CPC ............................ C07D 213/80; C07D 213/803
See application file for complete search history.

(56) References Cited

U.S. PATENT DOCUMENTS

2009/0163545 A1*   6/2009   Goldfarb .............. A61K 31/122
                                                                                514/312

FOREIGN PATENT DOCUMENTS

| CN | 101001862 | 7/2007 |
| CN | 101704780 | 5/2010 |
| CN | 103265478 | 8/2013 |
| WO | 2011006158 | 1/2011 |
| WO | 2012116010 | 8/2012 |

OTHER PUBLICATIONS

Dayam et al., 51(5) J. Med. Chem. 1136-1144 (2008) (CAS Abstract).*
Yakovlev et al., 31(11) Khimiko-Farmatsevticheskii Zhurnal 44-47 (1997) (CAS Abstract).*
Galam et al., 15(5) Bioorg. & Med. Chem. 1939-1946 (2007) (Year: 2007).*
Zhu et al., 76(4) Chem. Bio. & Drug Design 330-339 (2010) (Year: 2010).*
Anne et al., "Development of Potential Inhibitors of Botulinum Neurotoxin Type B", J. Med. Chem., 2003, pp. 4648-4656.
Salzameda et al., "A Cross-Over Inhibitor of the Botulinum Neurotoxin Light Chai B: A Natural Product Implicating an Exosite Mechanism of Action", Chem Commun, Feb. 14, 2011, pp. 1713-1715.
Pang et al., "Potent New Small-Molecule Inhibitor of Botulinum Neurotoxin Serotype A Endopeptidase Developed by Synthesis-Based Computer-Aided Molecular Design", Plos One, vol. 4, Issue 11, Nov. 10, 2009, pp. 1-18.
Eubanks et al., "Identification of a Natural Product Antagonist Against the Botulinum Neurotoxin Light Chain Protease", ACS Med Chem Lett., vol. 1, Issue 6, 2010, pp. 268-272.
Ruge et al., "Detection of Six Serotypes of Boulinum Neurotoxin Using Fluorogenic Reporters", Analytical Biochemistry, 2011, pp. 200-209.
Li et al., "High-Level Expression, Purification, and Characterization of Recombinant Type A Botulinum Neurotoxin Light Chain" Protein Expression and Purification, vol. 17, 1999, pp. 339-344.
Gilsdorf et al., "Expression, Purification, and Characterization of Clostridium Botulinum Type B Light Chain", Protein Expression and Purification, vol. 46, 2006, pp. 256-267.
Agarwal et al., "Cloning, High Level Expression, Purification, and Crystallization of the Full Length Clostridium Botulinum Neurotoxin Type E Light Chain", Protein Expression and Purification, vol. 34, 2004, pp. 95-102.
Yang et al., "Purification and Properties of Clostridium Botulinum Type F Toxin", Applied Microbiology, vol. 29, No. 5, May 1975, pp. 598-603.

(Continued)

*Primary Examiner* — Timothy R Rozof
(74) *Attorney, Agent, or Firm* — Melvin Li; Heslin Rothenberg Farley & Mesiti PC

(57) ABSTRACT

The present invention discloses a class of mercaptonicotinic acid compound and preparation method and use thereof; the general structural formula of the compound is as shown in Formula I. Experiment demonstrates that the mercaptonicotinic acid compound could inhibit activity of botulinum toxin endopeptidase and tetanus toxin endopeptidase in vitro, which has a significant protective effect on botulinum toxin poisoning in mice, and can be used for preparing medicine intended to prevent and/or treat botulism, as well as to prevent botulinum toxin exposure and tetanus.

9 Claims, No Drawings

(56) References Cited

OTHER PUBLICATIONS

Tonello, et al., "Recombinant and Truncated Tetanus Neurotoxin Light Chain: Cloning, Expression, Purification, and Proteolytic Activity", vol. 15, 1999, pp. 221-227.

Malizio, et al. "Purification of Clostridium Botulinum Type A Neurotoxin" Methods in Molecular Biology, vol. 145, pp. 27-39.

Ernest J. Bowmer, M.C., MD., "Preparation and Assay of the International Standards for Clostridium Botulinum Types A, B, C, D and E Antitoxins", Bull. Wld Hlth Org., 1963, vol. 29, pp. 701-709.

Armitsu et al., "Purification of Fully Activated Clostridium Botulinum Serotype B Toxin for Treatment of Patients with Dystonia", American Society for Microbiology, vol. 71, No. 3, Mar. 2003, pp. 1599-1603.

Xiaohe et al., "Synthesis, Biological Evaluation and Molecular Modeling Studies of N-aryl-2-arylthioacetamides as Non-nucleoside HIV-1 Reverse Transcriptase Inhibitors", Chem Biol Drug Des, vol. 76, 2010, pp. 330-339.

Galam et al., "High-Throughout Assay for the Identification of Hsp90 Inhibitors Based on Hsp90-Dependent Refolding of Firefly Luciferase", Bioorganic & Medicinal Chemistry, vol. 15, 2007, pp. 1939-1946.

Dayam et al., "Quinolone 3-Carboxylic Acid Pharmacophore: Design of Second Generation HIV-1 Integrase Inhibitors", J. Med. Chem., vol. 51, 2008, pp. 1136-1144.

STN Columbus, 444161-23-3 Registry, Entered STN: Aug. 19, 2002.

STN Columbus, 329078-82-2 Registry, Entered STN: Mar. 27, 2001.

International Preliminary Report on Patentability in Application No. PCT/CN2014/077768, dated Nov. 24, 2015, pp. 1-18.

* cited by examiner

MERCAPTONICOTINIC ACID COMPOUND AND PREPARATION METHOD AND USE THEREOF

CROSS REFERENCE TO RELATED APPLICATIONS

This application is a national stage filing under 35 U.S.C. § 371 of International Application No. PCT/CN2014/077768 filed on May 19, 2014, and published in Chinese on Nov. 27, 2014 as WO 2014/161405 A1, claiming priorities from Chinese Patent Application Nos. 201310188043.2 and 201310187415.X, both of which filed on May 5, 2013, the disclosure of these applications being hereby incorporated herein by reference and in their entirety.

FIELD OF THE INVENTION

The present invention belongs to the field of medicine, and in particular is concerned with a class of mercaptonicotinic acid compounds and method of manufacture and use thereof.

BACKGROUND OF THE INVENTION

*Clostridium* neurotoxin includes *Clostridium botulinum* neurotoxin and *Clostridium* tetanus toxin.

*Clostridium botulinum* neurotoxins (hereinafter referred to botulinum toxin) is a group of proteins known to have the highest toxicity (including types A-G), and is produced primarily by *Clostridium botulinum* in anaerobic condition. It mainly inhibits nerve ending from releasing acetylcholine, causing muscle relaxation and paralysis, especially paralysis in respiratory muscles as a major cause of death. For type A botulinum toxin in aerosol, the lethal dose of inhalation to human is 0.3 µg, LCt50 is 0.1-0.5 mg·min/m3, lethal dose of intravenous injection is 0.15-0.3 µg, and lethal dose of oral administration is 8-10 µg. Botulism may happen in many ways, including when botulinum toxin aerosol released in an environment (botulinum toxin exposure), causing respiratory inhalation poisoning. Due to technical limitations, releasing aerosol in a large scale does not happen easily. Currently, the main routes of poisoning are food contamination and contracting toxin by water passing through the digestive tract. Occasionally, would infection leads to poisoning (botulinum toxin poisoning). In addition, type A botulinum toxin has been widely used in the clinical treatment of cholinergic nerve and muscle dysfunction, as well as to eliminate wrinkles in cosmetic practices. During use in treatment, botulism symptoms may occur due to overdose, misuse, abuse, and/or adverse reaction. Botulism have relatively short incubation period, fast progression, relatively severe state of illness, and high mortality. Poisoning in human is mainly caused by botulinum toxin of types A, B, E, and F, in that types A and B have the highest neurotoxicity to human.

*Clostridium* tetanus toxin is produced by *Clostridium tetani* in anaerobic condition, which has high affinity to spinal anterior horn cells and brain stem cells, and could prevent releasing of inhibitory neurotransmitter from presynaptic membrane, thereby causing symptoms such as intense muscle spasm, cardiac arrhythmia and respiratory failure, etc. Wound infection is the main way to cause tetanus, when the body sustains a trauma and the wound is contaminated, *Clostridium tetani* can invade local wound surface causing exogenous infection, and with bacteria propagating at local site, releasing toxin, and causing tetanus.

Currently, antitoxin horse serum is used for prevention and treatment of exposure to Botulinum Neurotoxins or Tetanus toxin, botulism and tetanus. It is effective for more than 80% of poisoned patients. However, this type of medicine has significant side effects, with severe hypersensitivity reaction (including anaphylactic and anaphylactoid reactions) and delayed anaphylactic reaction (serum sickness) possibly occurring after administration of the antitoxin. Clinical reports show about 9% of cases experience serum sickness and anaphylactic reaction. In addition, antitoxin is produced from horse plasma, which may have the risk of carrying pathogens such as virus. These disadvantages limit wide application of antitoxin horse serum, and raise demand for development of new type of medicine.

*Clostridium botulinum* neurotoxin and *Clostridium* tetanus toxin share similar pathogenic process in that the C-terminus of heavy chain of toxin binds to the ganglioside on the membrane of the nerve cells, rearranges its structure in acidic environment, and promotes N-terminus of heavy chain entering into membrane. Meanwhile, the light chain unfolds and the disulfide bond is reduced and transferred into cells as zinc ion metalloenzyme, catalytically cracking a class of intracellular substrate proteins (types A and E *Clostridium botulinum* neurotoxin act on synaptosome associated protein SNAP-25, while types B, D, F, and G *Clostridium botulinum* neurotoxin and *Clostridium* tetanus toxin act on synaptic vesicle associated membrane protein VAMP), thereby affecting the transfer of acetylcholine and intervening conduction of nerve impulse, so as to cause paralysis or excitement of motor nerve. If one or more aspects of binding, cytosis and catalysis is/are inhibited or repressed, the neurotoxicity of toxin can be suppressed effectively. Targeting design of light chain of toxin having enzymatic activity and development of inhibitor are the hot spot of researches recently.

Harry B et al. performed in vitro high-throughput screening of natural extract from plants, marine tissue, and fungus for substance inhibiting *clostridium* toxin, found 30 non-subtype inhibitors, of which 5 extracts can suppressed both types B and E botulinum toxin. Anne C et al. developed a class of highly reactive sulfur-containing peptide compounds, wherein Ki value of the compound with the highest activity to light chain of type B botulinum toxin was up to 2.3 nM, but follow-up report on overall activity in animals is not seen (Reference 1: Anne C, et al. *J Med Chem*, 2003, 46:4648-4656). Salzameda N T et al. 2011 found, L-cichoric acid significantly inhibited light chain of type B botulinum toxin, and the compound had certain inhibitory activity on subtype A (reference 2: Salzameda N T, et al. Chem Commun, 2011, 47:1713-1715), the activity was relatively weak. Pang, Y.-P. et al. 2009 found that AHP, an azole-based compound, was a potential inhibitor, which could effectively neutralize toxicity of type A botulinum toxin on N2a cells through binding to Zn catalytic region in the large hydrophobic region pocket of the active site of type A botulinum toxin light chain (reference 3: Pang, Y.-P. et al. PLos One 2009, 4, e7730.), but still no in vivo activity has been reported. Eubanks, L. M. et al. 2010 found that lomofungin could inhibit light chain of type A botulinum toxin (Ki value 6.7±0.7 uM), showing a typical non-competitive dynamics, but the compound had multiple unstable phenolic hydroxyl groups and aldehyde groups (reference 4: Eubanks, L. M., et al. ACS Med. Chem. Lett. 2010, 1:268-272.).

Focusing on the shortcomings of the inhibiting compound candidates that have been developed, there is a need to develop a class of active compounds which potentially have wider spectrum of in vitro inhibition and antagonism against *clostridium* neurotoxin (multiple types of botulinum toxin and *clostridium* tetanus toxin), and which can pose a higher anti-poisoning activity among all animal species, while providing better pharmaceutical efficacy, from which new medicine can be developed therefrom.

DESCRIPTION OF THE INVENTION

The present invention aims at providing a class of mercaptonicotinic acid compounds and pharmaceutically acceptable salts, esters, solvates thereof. Another object of the present invention is to provide preparation methods of this class of compounds and pharmaceutically acceptable salts, esters, solvates thereof. A third object of the present invention is to provide medicinal application of this class of compounds and pharmaceutically acceptable salts, esters, solvates thereof.

A first aspect of the present invention is to provide a class of mercaptonicotinic acid compounds and pharmaceutically acceptable salts, esters, solvates thereof, and the general structural formula of the compound is shown as Formula I:

(Formula I)

In Formula I:

$R_1$, $R_2$, $R_3$, and $R_4$ independently represent any of the following groups: hydrogen, hydroxy, amino, halogen, cyano, hydrazino, azido, lower alkylamino, lower alkyl, lower haloalkyl, cycloalkyl, lower alkoxy, lower haloalkoxy, lower alkenyl, lower cyanoalkyl, lower nitroalkyl, acylamino, lower acylamino alkyl, lower hydrazino alkyl, lower azido alkyl, $(CH_2)_m NR_7 R_8$, $(CH_2)_m OR_9$, $(CH_2)_m SR_9$, $(CH_2)_m NR_7 C(O)R_9$, $(CH_2)_m C(O)R_9$, $(CH_2)_m OC(O)R_9$, $O(CH_2)_m NR_7 R_8$, $OC(O)NR_7$, $OC(O)(CH_2)_m OC(O)R_9$;

Or, a 5- or 6-membered ring is formed between $R_1$, $R_2$, and the carbon atoms attaching $R_1$ and $R_2$ in the benzene ring;

Or, a 5- or 6-membered ring is formed between $R_2$, $R_3$, and the carbon atoms attaching $R_2$ and $R_3$ in the benzene ring;

Or, a 5- or 6-membered ring is formed between $R_3$, $R_4$, and the carbon atoms attaching $R_3$ and $R_4$ in the benzene ring;

The unit forming the 5- or 6-membered ring is selected from CH, $CH_2$, O, S or $NR_7$;

$R_5$ and $R_6$ independently represent any of the following groups: hydrogen, hydroxy, amino, halogen, cyano, hydrazino, azido, lower alkylamino, lower alkyl, lower haloalkyl, lower alkoxy, lower alkenyl and $(CH_2)_m COOH$;

$R_7$, $R_8$, and $R_9$ independently represent hydrogen, lower alkyl, or cycloalkyl;

m is an integer between 0 and 3;

In the present invention, the term "lower" associated with alkyl and alkoxy refers to a linear- or branched-chain saturated aliphatic alkyl group containing 1-6 carbon atoms, for example: methyl, ethyl, propyl, isopropyl, butyl, t-butyl, methoxy and ethoxy; the term "lower" associated with alkenyl refers to a group containing 2-6 carbon atoms and one or more double bond, for example: vinyl, allyl, iso-allyl, pentenyl, hexenyl, and propenyl. The term "cycloalkyl" refers to a ring containing 3-7 carbon atoms, for example: cyclopropyl, cyclobutyl, cyclopentyl or cyclohexyl. The term "halogen" refers to chlorine, bromine, iodine or fluorine. Groups of terms lower haloalkyl, lower cyanoalkyl, lower nitroalkyl, lower acylamino alkyl, lower hydrazino alkyl, and lower azido alkyl are substituted by one to three halogen, cyano, nitro, acylamino, hydrazine, and azido, respectively. Lower alkylamino contains one or two lower alkyl, for example, representing $NHCH_3$, $NHCH_2CH_3$, $N(CH_3)_2$ or $CH_3NCH_2CH_3$.

Preferably, in Formula I:

$R_1$, $R_2$, $R_3$, and $R_4$ independently represent any of the following groups: hydrogen, hydroxy, amino, halogen, lower alkyl, lower haloalkyl, lower alkoxy, and lower haloalkoxy;

$R_5$ and $R_6$ independently represents: hydrogen or $(CH_2)_m COOH$;

m is an integer between 0 and 3;

More preferably, compounds shown in Formula I are selected from the following compounds:

2-(2-(5-chloro-2-methoxyanilino)acetylthio)nicotinate sodium,
2-(2-(5-chloro-2-methoxyanilino)acetylthio)nicotinic acid,
2-(2-(5-chloro-2-methoxyanilino)acetylthio)nicotinate potassium,
2-(2-(3-chloro-5-methoxyanilino)acetylthio)nicotinate sodium,
2-(2-(2-ethoxyanilino) acetylthio)nicotinic acid,
2-(2-(5-chloro-2-ethoxyanilino)acetylthio)nicotinic acid,
2-(2-(5-chloro-2-propoxyanilino)acetylthio)nicotinic acid,
2-(2-(2-chlorophenyl)acetylthio)nicotinate potassium,
2-(2-(2,5-dibromoanilino)acetylthio)nicotinate potassium,
2-(2-(4-chlorophenyl)acetylthio)nicotinate potassium,
2-(2-(2,5-dichlorophenyl)acetylthio)nicotinate potassium,
2-(2-(4-bromoanilino)acetylthio)nicotinate potassium,
2-(2-(5-fluoro-2-methoxyanilino)acetylthio)nicotinate potassium,
2-(2-(5-methoxy-2-chlorophenyl)acetylthio)nicotinate potassium,
2-(2-(5-chloro-2-methoxyanilino)acetylthio)isonicotinate potassium,
2-(2-(2,5-dimethoxyanilino)acetylthio)nicotinate potassium,
2-(anilino-2-acetylthio)nicotinic acid,
2-(2-(5-fluoro-2-chlorophenyl)-2-acetylthio)nicotinate potassium,
2-(2-(4-fluoroanilino)acetylthio)nicotinate potassium,
2-(2-(5-chlorophenyl)acetylthio)nicotinate potassium,
2-(2-(4-trifluoromethoxyanilino)acetylthio)nicotinate potassium,
2-(2-(2,5-difluoroanilino)acetylthio)nicotinate potassium,
2-(2-(5-chloro-2-benzyloxyanilino)acetylthio)nicotinate sodium,
2-(2-(2-trifluoromethoxyanilino)acetylthio)nicotinate potassium,
2-(2-(5-trifluoromethoxyanilino)acetylthio)nicotinate potassium,
2-(2-(5-trifluoromethoxy-2-bromoanilino)acetylthio)nicotinate potassium, or
2-(2-(5-fluoro-2-ethoxyanilino)acetylthio)nicotinic acid.

Pharmaceutically acceptable salts of compounds shown in Formula I may be various salts formed by substitution of carboxyl group and metal ion or amino compound on a pyridine ring. The salt can be a salt formed with inorganic or organic acid, wherein salts formed with inorganic acids are hydrochloride, sulfate, phosphate, diphosphate, hydrogen phosphate, hydrobromide or nitrate, etc; and salts formed with organic acids are acetate, maleate, fumarate, tartrate, succinate, lactate, citrate, p-toluenesulfonate, salicylate, oxalate, palmitate or stearate, etc.

Pharmaceutically acceptable esters of compounds shown in Formula I refer to those can hydrolyze in vivo, and include esters that are prone to decompose to its parent compounds or salts in human body, such as C1-C6 alkyl ester, etc.

Pharmaceutically acceptable solvates of compounds shown in Formula I refer to solvates formed with pharmaceutically acceptable solvent, such as water, alcohol, DMSO, etc.

A second aspect of the present invention is to provide preparation methods of mercaptonicotinic acid compounds described above and pharmaceutically acceptable salts, esters, solvates thereof, wherein the preparation of the compound shown in Formula I comprises following steps:

A) Compound shown in Formula II is made to react with chloroacetyl chloride or chloroacetyl bromide, to yield compound shown in Formula III;

(Formula II)

(Formula III)

Definitions of $R_1$, $R_2$, $R_3$ and $R_4$ in Formula II, Formula III are the same as Formula I;

B) Compound shown in Formula III is made to react with compound shown in Formula IV, to yield compound shown in Formula I;

(Formula IV)

Definitions of $R_5$, $R_6$ in Formula IV are the same as Formula I.

A third aspect of the present invention is to provide an application of mercaptonicotinic acid compounds above and pharmaceutically acceptable salts, esters, solvates thereof in medicine preparation.

A first application provided by the present invention is the application of mercaptonicotinic acid compounds shown in Formula I, and pharmaceutically acceptable salts, esters, solvates, or their mixtures, preparations thereof, in preparing medicine to prevent and/or treat botulinum toxin poisoning, or medicine to prevent botulinum toxin exposure.

A second application provided by the present invention is the application of mercaptonicotinic acid compounds shown in Formula I, and pharmaceutically acceptable salts, esters, solvates, or their mixtures thereof, in preparing inhibitor of botulinum toxin endopeptidase.

A third application provided by the present invention is the application of mercaptonicotinic acid compounds shown in Formula I, and pharmaceutically acceptable salts, esters, solvates, or their mixtures thereof, in preparing medicine to prevent and/or treat tetanus.

A fourth application provided by the present invention is the application of mercaptonicotinic acid compounds shown in Formula I, and pharmaceutically acceptable salts, esters, solvates, or their mixtures thereof, in preparing inhibitor of *Clostridium* tetanus toxin endopeptidase.

Said botulinum toxin in the present invention includes type A botulinum toxin, type B botulinum toxin, type E botulinum toxin, type F botulinum toxin.

Medicines prepared with compounds shown in Formula I, and pharmaceutically acceptable salts, esters, solvates, or mixture thereof as active ingredient, to prevent and/or treat botulinum toxin poisoning, to prevent botulinum toxin exposure, and to prevent and/or treat tetanus, are within the scope of the present invention.

Said medicines can be delivered to body such as muscular, intradermal, subcutaneous, intravenous, and mucosal tissues by means of injection, spray, nasal drop, eye drop, infiltration, absorption, physical or chemical mediation, or after being mixed or encapsulated with other substances.

If needed, one or more pharmaceutically acceptable carriers can also be added into above-mentioned medicines. Said carriers include conventional diluents, excipients, fillers, binders, humectants, disintegrants, absorption promoters, surfactants, adsorption carriers, lubricants, etc. in the pharmaceutical field.

Said medicines can be formulated as various forms including injections, suspensions, powders, tablets, granules, etc. Medicine in various dosage forms described above can be prepared according to conventional methods in the pharmaceutical field.

Pharmacodynamic studies have showed that mercaptonicotinic acid compounds proposed in the present invention cab inhibit activity of botulinum toxin endopeptidase and tetanus toxin endopeptidase in vitro, while having significant protective effect in a botulinum toxin poisoned mice. Medicine and preparations proposed can have a wider range of inhibition and antagonism against *Clostridium* neurotoxin in vitro (multiple types of botulinum toxin and *Clostridium* tetanus toxin), and can pose a higher anti-poisoning activity among all animal species.

ILLUSTRATED EXAMPLES

The present invention will be further described below with specific embodiments. It should be understood that the following embodiments are used to explain the present invention only, but not intended to limit the scope of the invention.

Unless otherwise specified, all experimental methods described in the following embodiments are conventional.

Reagents and materials recited, unless otherwise specified, all are commercially available.

Example 1. Synthesis of 2-(2-(5-chloro-2-methoxyanilino)acetylthio)nicotinate sodium (Formula I-1)

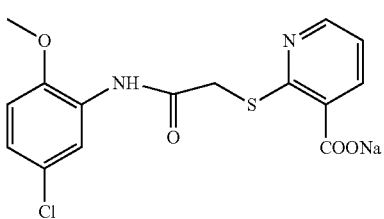
(Formula I-1)

3.14 g (0.02 mol) 2-methoxy-5-chloroaniline was dissolved in 30 ml of cold acetic acid, 2.5 g (0.02 mol) of chloroacetyl chloride was added dropwisely, and it was stirred at room temperature overnight. The reaction mixture was then poured into 50 ml of iced water, and stirred for 1 hour. Solid was precipitated, filtered, washed with water, and dried to yield the crude product.

Product from the previous step and 1.55 g (0.01 mol) 2-mercapto-nicotinic acid were added to a mixed solution of 25 ml of THF in water (volume ratio 1:1). After it was cooled to 0° C., 1.6 g of sodium hydroxide was added, and the mixture was allowed to react while stirring, heated to room temperature, stirred overnight. Large amount of solid was precipitated, filtered, washed with water, dried to produce 3.55 g off-white solid, with a yield of 86%.

Results of structural verification was as follows:
1H-NMR (DMSO-d6): 10.08 (s, 1H), 8.48-8.50 (m, 1H), 8.28 (d, 1H), 8.14-8.16 (m, 1H), 7.20-7.22 (m, 1H), 7.02-7.04 (m, 1H), 6.98 (d, 1H), 3.79 (s, 2H), 3.74 (s, 3H). EI-MS: m/z: 353.2 [M+H]$^+$.

After identification, the product obtained was indeed the target compound of Formula I-1.

Example 2. Synthesis of 2-(2-(5-chloro-2-methoxyanilino)acetylthio)nicotinic Acid (Formula I-2)

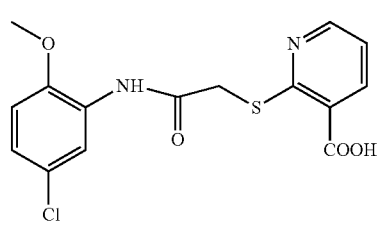
(Formula I-2)

2-(2-(5-chloro-2-methoxyanilino)-2-acetylthio)nicotinate sodium prepared in Example 1 was placed into water, and then the pH is adjusted to 2 with 1M hydrochloric acid, filtered, washed with water, and dried to get white solid, with a yield of 97%.

Results of structural verification were as following:
1H-NMR (DMSO-d6): 13.56 (s, 1H), 9.75 (s, 1H), 8.69-8.70 (m, 1H), 8.29-8.30 (m, 1H), 8.19 (d, 1H), 7.35-7.37 (m, 1H), 7.01-7.08 (m, 2H), 4.02 (s, 2H), 3.79 (s, 3H). EI-MS: m/z: 375.4 [M+H]+.

After identification, the product obtained was indeed the target compound of Formula I-2.

Example 3. Synthesis of 2-(2-(5-chloro-2-methoxyanilino)acetylthio)nicotinate potassium (Formula I-3)

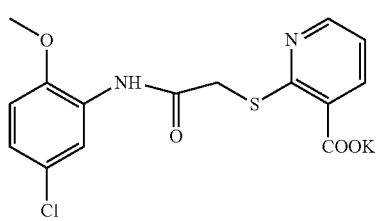
(Formula I-3)

3.14 g 2-methoxy-5-chloroaniline was dissolved in 30 ml of cold acetic acid, 2.5 g of chloroacetyl chloride was added in a dropwise manner, and it was stirred at room temperature overnight. The reaction solution was then poured into 50 ml of icy water, and stirred for 1 hour. Solid was precipitated, filtered, washed with water, and dried to yield the crude product.

Product from the previous step and 1.55 g 2-mercaptonicotinic acid were added to a mixed solution of 25 ml THF in water (volume ratio 1:1). After it was cooled to 0° C., 2.0 g of potassium hydroxide was added. The mixture was allowed to react while stirring, heated to room temperature, and stirred overnight. Large amount of solid was precipitated, filtered, washed with water, and dried to get 2.62 g off-white solid, with a yield of 67%.

Results of structural verification were as follows:
1H-NMR (DMSO-d6): 9.93 (s, 1H), 8.57-8.58 (m, 1H), 8.24 (d, 1H), 8.19-8.21 (m, 1H), 7.26-7.28 (m, 1H), 6.99-7.06 (m, 2H), 3.89 (s, 2H), 3.77 (s, 3H). EI-MS: m/z: 391.4 [M+H]$^+$.

After identification, the product obtained was indeed the target compound of Formula I-3.

Example 4. Synthesis of 2-(2-(3-chloro-5-methoxyanilino)acetylthio)nicotinate sodium (Formula I-4)

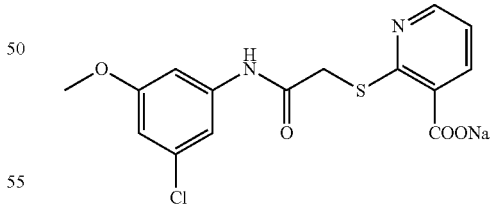
(Formula I-4)

With reference to the Example 1, 2-methoxy-5-chloroaniline was replaced with 3-methoxy-5-chloroaniline, with a yield of 77%.

Results of structural verification were as follows:
1H-NMR (DMSO-d6): 9.97 (s, 1H), 8.48-8.51 (m, 1H), 8.25 (d, 1H), 8.12-8.15 (m, 1H), 7.32 (s, 1H), 7.05 (s, 1H), 6.95 (s, 1H), 3.77 (s, 2H), 3.71 (s, 3H). EI-MS: m/z: 353.0[M+H]$^+$.

After identification, the product obtained was indeed the target compound of Formula I-4.

Example 5. Synthesis of 2-(2-(2-ethoxyanilino)acetylthio)nicotinic Acid (Formula I-5)

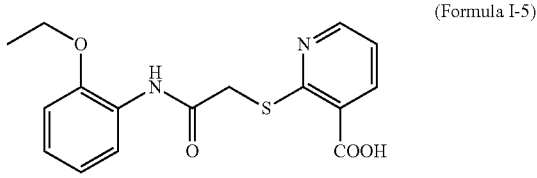 [SMILES: CCOc1ccccc1NC(=O)CSc1ncccc1C(=O)O]
(Formula I-5)

With reference to the Example 1 and 2, 2-methoxy-5-chloroaniline was replaced with 2-ethoxyaniline, with a yield of 84%.

Results of structural verification were as following:
1H-NMR (DMSO-d6): 13.63 (s, 1H), 9.31 (s, 1H), 8.66 (d, 1H), 8.29 (d, 1H), 8.10 (d, 1H), 7.31-7.33 (m, 1H), 6.95-6.99 (m, 2H), 6.86-6.88 (m, 1H), 3.97-4.02 (m, 4H), 1.16 (t, 3H). EI-MS: m/z: 333.3 [M+H]$^+$.

After identification, the product obtained was indeed the target compound of Formula I-5.

Example 6. Synthesis of 2-(2-(5-chloro-2-ethoxyanilino)acetylthio)nicotinic Acid (Formula I-6)

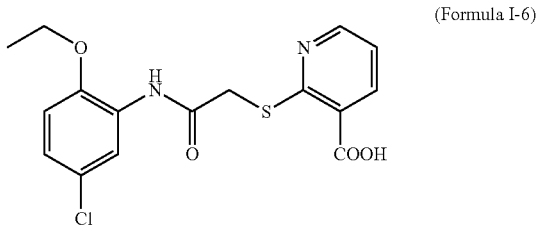 [SMILES: CCOc1ccc(Cl)cc1NC(=O)CSc1ncccc1C(=O)O]
(Formula I-6)

With reference to the Example 1 and 2, 2-ethoxy-5-chloroaniline was replaced with 2-methoxy-5-chloroaniline, with a yield of 82%.

Results of structural verification were as follows:
1H-NMR (DMSO-d6): 13.60 (s, 1H), 9.43 (s, 1H), 8.64-8.66 (m, 1H), 8.28-8.30 (m, 1H), 8.18 (d, 1H), 7.32-7.34 (m, 1H), 6.98-7.05 (m, 2H), 4.00-4.04 (m, 4H), 1.17 (t, 3H). EI-MS: m/z: 367.3 [M+H]+.

After identification, the product obtained was indeed the target compound of Formula I-6.

Example 7. Synthesis of 2-(2-(5-chloro-2-propoxyanilino)acetylthio)nicotinic Acid (Formula I-7)

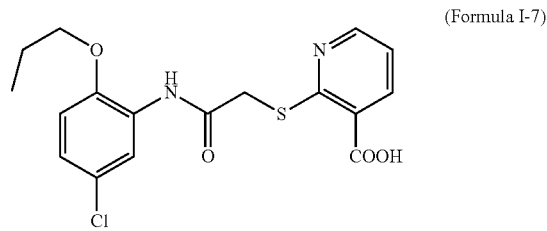 [SMILES: CCCOc1ccc(Cl)cc1NC(=O)CSc1ncccc1C(=O)O]
(Formula I-7)

With reference to the Example 1 and 2, 2-methoxy-5-chloroaniline was 2-propoxy-5-chloroaniline was replaced with, with a yield of 80%.

Results of structural verification were as follows:
1H-NMR (DMSO-d6): 13.60 (s, 1H), 9.37 (s, 1H), 8.62-8.64 (m, 1H), 8.28-8.30 (m, 1H), 8.20 (d, 1H), 7.31-7.33 (m, 1H), 7.00-7.05 (m, 2H), 4.02 (s, 2H), 3.91 (t, 2H), 1.54-1.57 (m, 2H), 0.81 (t, 3H). EI-MS: m/z: 381.4 [M+H]$^+$.

After identification, the product obtained was indeed the target compound of Formula I-7.

Example 8. Synthesis of 2-(2-(2-chlorophenyl)acetylthio)nicotinate potassium (Formula I-8)

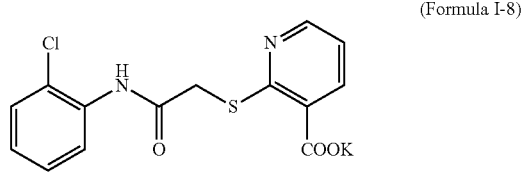
(Formula I-8)

With reference to the Example 3, 2-methoxy-5-chloroaniline was replaced with 2-chloroaniline, with a yield of 85%.

Results of structural verification were as follows:
1H-NMR (DMSO-d6): 9.83 (s, 1H), 8.41-8.43 (m, 1H), 8.05-8.10 (m, 2H), 7.41-7.44 (m, 1H), 7.26-7.32 (m, 1H), 7.05-7.13 (m, 2H), 3.79 (s, 2H). EI-MS: m/z: 363.2 [M+H]$^+$.

After identification, the product obtained were indeed the target compound of Formula I-8.

Example 9. Synthesis of 2-(2-(2,5-dibromoanilino)acetylthio)nicotinate potassium (Formula I-9)

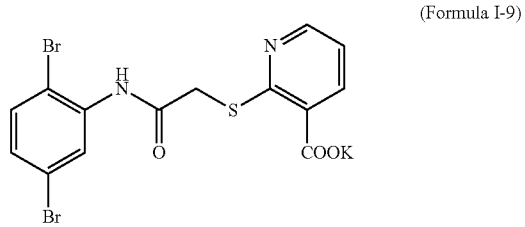
(Formula I-9)

With reference to the Example 3, 2-methoxy-5-chloroaniline was replaced with 2,5-dibromoaniline, with a yield of 87%.

Results of structural verification were as follows:
1H-NMR (DMSO-d6): 9.76 (s, 1H), 8.44-8.47 (m, 1H), 8.24 (d, 1H), 8.05-8.08 (m, 1H), 7.54 (d, 1H), 7.08-7.22 (m, 2H), 3.79 (s, 2H). EI-MS: m/z: 385.1 [M+H]$^+$.

After identification, the product obtained was indeed the target compound of Formula I-9.

Example 10. Synthesis of 2-(2-(4-chlorophenyl)acetylthio)nicotinate potassium (Formula I-10)

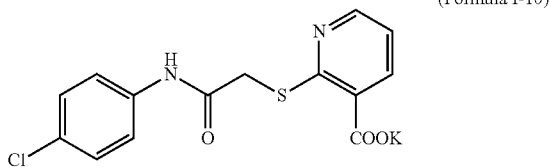
(Formula I-10)

With reference to the Example 3, 2-methoxy-5-chloroaniline was replaced with 4-chloroaniline, with a yield of 83%.

Results of structural verification were as follows: 1H-NMR (DMSO-d6): 10.38 (s, 1H), 8.30-8.33 (m, 1H), 8.00-8.03 (m, 1H), 7.62 (d, 2H), 7.31 (d, 2H), 7.01-7.05 (m, 1H), 3.79 (s, 2H). EI-MS: m/z: 362.6 $[M+H]^+$.

After identification, the product obtained was indeed the target compound of Formula I-10.

Example 11. Synthesis of 2-(2-(2,5-dichlorophenyl)acetylthio)nicotinate potassium (Formula I-11)

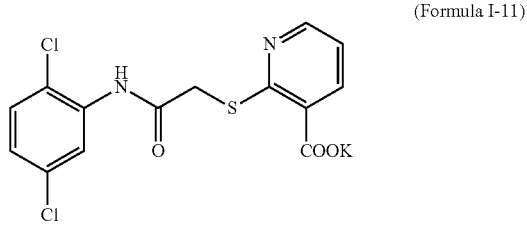
(Formula I-11)

With reference to the Example 3, 2-methoxy-5-chloroaniline was replaced with 2,5-dichloroaniline, with a yield of 86%.

Results of structural verification were as follows: 1H-NMR (DMSO-d6): 9.97 (s, 1H), 8.42-8.44 (m, 1H), 8.21 (m, 1H), 8.08 (d, 1H), 7.47 (d, 1H), 7.10-7.17 (m, 2H), 3.82 (s, 2H). EI-MS: m/z: 396.1 $[M+H]^+$.

After identification, the product obtained was indeed the target compound of Formula I-11.

Example 12. Synthesis of 2-(2-(4-bromoanilino)acetylthio)nicotinate potassium (Formula I-12)

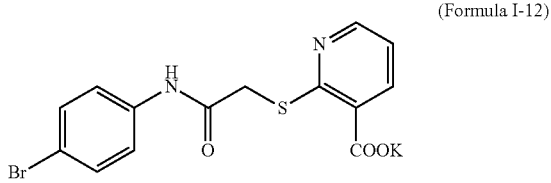
(Formula I-12)

With reference to the Example 3, 2-methoxy-5-chloroaniline was replaced with 4-bromoaniline, with a yield of 85%.

Results of structural verification were as following: 1H-NMR (DMSO-d6): 10.42 (s, 1H), 8.31-8.33 (m, 1H), 8.4 (d, 1H), 7.57 (d, 2H), 7.44 (d, 2H), 7.01-7.05 (m, 1H), 3.86 (s, 2H). EI-MS: m/z: 405.4 $[M+H]^+$.

After identification, the product obtained was indeed the target compound of Formula I-12.

Example 13. Synthesis of 2-(2-(5-fluoro-2-methoxyanilino)acetylthio)nicotinate potassium (Formula I-13)

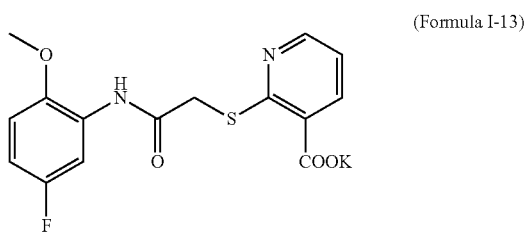
(Formula I-13)

With reference to the Example 3, 2-methoxy-5-chloroaniline was replaced with 4-fluoroaniline, with a yield of 82%.

Results of structural verification were as following: 1H-NMR (DMSO-d6): 9.97 (s, 1H), 8.55-8.57 (m, 1H), 8.20-8.23 (d, 1H), 8.01-8.06 (m, 1H), 7.24-7.28 (m, 1H), 6.94-6.99 (m, 1H), 6.78-6.84 (m, 1H), 3.87 (s, 2H), 3.73 (s, 3H). EI-MS: m/z: 375.3 $[M+H]^+$.

After identification, the product obtained was indeed the target compound of Formula I-13.

Example 14. Synthesis of 2-(2-(5-methoxy-2-chlorophenyl)acetylthio)nicotinate potassium (Formula I-14)

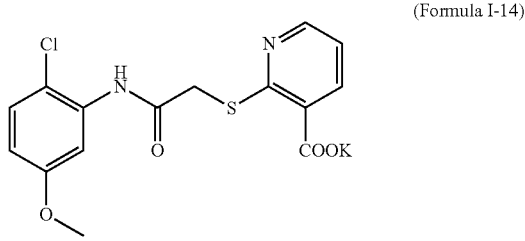
(Formula I-14)

With reference to the Example 3, 2-methoxy-5-chloroaniline was replaced with 5-methoxy-2-chloroaniline, with a yield of 87%.

Results of structural verification were as follows: 1H-NMR (DMSO-d6): 9.78 (s, 1H), 8.41-8.44 (m, 1H), 8.06-8.10 (m, 1H), 7.81 (d, 1H), 7.30-7.32 (m, 1H), 7.09-7.13 (m, 1H), 6.65-6.69 (m, 1H), 3.79 (s, 2H), 3.71 (s, 3H). EI-MS: m/z: 391.4 $[M+H]^+$.

After identification, the product obtained was indeed the target compound of Formula I-14.

Example 15. Synthesis of 2-(2-(5-chloro-2-methoxyanilino)acetylthio)isonicotinate potassium (Formula I-15)

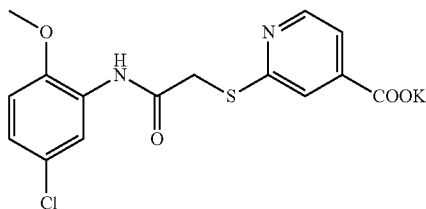
(Formula I-15)

With reference to the Example 3, 2-mercaptonictinic acid was replaced with 2-mercaptoisonictinic acid, with a yield of 79%.

Results of structural verification were as follows: 1H-NMR (DMSO-d6): 10.12 (s, 1H), 8.44 (d, 1H), 8.23 (d, 1H), 7.61 (s, 1H), 7.48 (d, 1H), 6.99-7.09 (m, 2H), 4.00 (s, 2H), 3.79 (s, 3H). EI-MS: m/z: 391.2 [M+H]$^+$.

After identification, the product obtained was indeed the target compound of Formula I-15.

Example 16. Synthesis of 2-(2-(2,5-dimethoxyanilino)acetylthio)nicotinate potassium (Formula I-16)

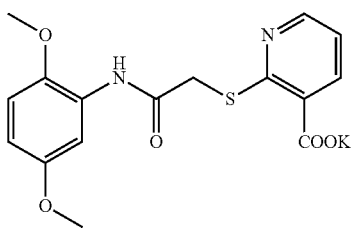
(Formula I-16)

With reference to the Example 3, 2-methoxy-5-chloroaniline was replaced with 2,5-dimethoxyaniline, with a yield of 87%.

Results of structural verification were as follows: 1H-NMR (DMSO-d6): 9.61 (s, 1H), 8.68-8.69 (m, 1H), 8.26-8.30 (m, 1H), 7.81 (d, 1H), 7.32-7.36 (m, 1H), 6.89 (d, 1H), 6.54-6.58 (m, 1H), 3.98 (s, 2H), 3.70 (s, 3H), 3.69 (s, 3H). EI-MS: m/z: 387.2 [M+H]$^+$.

After identification, the product obtained was indeed the target compound of Formula I-16.

Example 17. Synthesis of 2-(anilino-2-acetylthio)nicotinic Acid (Formula I-17)

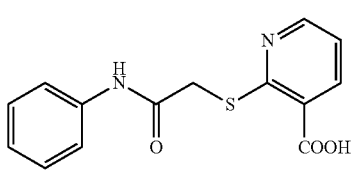
(Formula I-17)

With reference to the Example 3, 2-methoxy-5-chloroaniline was replaced with aniline, with a yield of 89%.

Results of structural verification were as following: 1H-NMR (DMSO-d6): 13.5 (s, 1H), 10.20 (s, 1H), 8.58-8.60 (m, 1H), 8.23 (d, 1H), 7.57 (d, 2H), 7.22-7.31 (m, 3H), 7.00-7.08 (m, 1H), 4.02 (s, 2H). EI-MS: m/z: 389.3 [M+H]$^+$.

After identification, the product obtained was indeed the target compound of Formula I-17.

Example 18. Synthesis of 2-(2-(5-fluoro-2-chlorophenyl)-2-acetylthio)nicotinate potassium (Formula I-18)

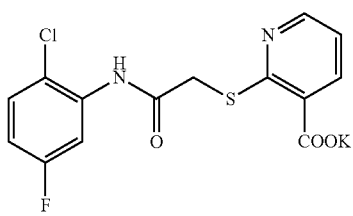
(Formula I-18)

With reference to the Example 3, 2-methoxy-5-chloroaniline was replaced with 5-fluoro-2-chloroaniline, with a yield of 75%.

Results of structural verification were as follows: 1H-NMR (DMSO-d6): 9.98 (s, 1H), 8.43-8.45 (m, 1H), 8.01-8.11 (m, 2H), 7.45-7.50 (m, 1H), 7.10-7.15 (m, 1H), 6.95-6.99 (m, 1H), 3.82 (s, 2H). EI-MS: m/z: 379.5 [M+H]$^+$.

After identification, the product obtained was indeed the target compound of Formula I-18.

Example 19. Synthesis of 2-(2-(4-fluoroanilino)acetylthio)nicotinate potassium (Formula I-19)

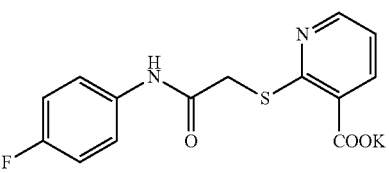
(Formula I-19)

With reference to the Example 3, 2-methoxy-5-chloroaniline was replaced with 4-fluoroaniline, with a yield of 79%.

Results of structural verification were as following: 1H-NMR (DMSO-d6): 10.29 (s, 1H), 8.32-8.34 (m, 1H), 8.00-8.03 (m, 1H), 7.57-7.62 (m, 2H), 7.01-7.13 (m, 3H), 3.78 (s, 2H). EI-MS: m/z: 345.5 [M+H]$^+$.

After identification, the product obtained was indeed the target compound of Formula I-19.

Example 20. Synthesis of 2-(2-(5-chlorophenyl)acetylthio)nicotinate potassium (Formula I-20)

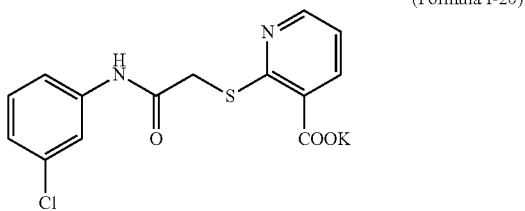
(Formula I-20)

With reference to the Example 3, 2-methoxy-5-chloroaniline was replaced with 5-chloroaniline, with a yield of 82%.

Results of structural verification were as follows: 1H-NMR (DMSO-d6): 10.47 (s, 1H), 8.31-8.33 (m, 1H), 8.01-8.04 (m, 1H), 7.81 (s, 1H), 7.43-7.46 (m, 1H), 7.27-7.32 (m, 1H), 7.01-7.07 (m, 2H), 3.79 (s, 2H). EI-MS: m/z: 361.3 $[M+H]^+$.

After identification, the product obtained was indeed the target compound of Formula I-20.

Example 21. Synthesis of 2-(2-(4-trifluoromethoxyanilino)acetylthio)nicotinate potassium (Formula I-21)

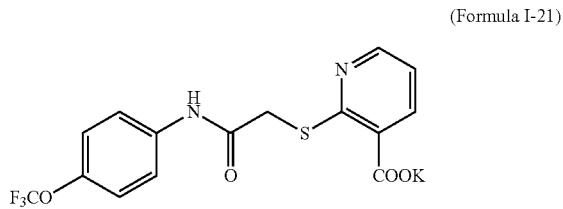
(Formula I-21)

With reference to the Example 3, 2-methoxy-5-chloroaniline was replaced with 4-trifluoromethoxyaniline, with a yield of 80%.

Results of structural verification were as following: 1H-NMR (DMSO-d6): 10.45 (s, 1H), 8.31-8.33 (m, 1H), 8.00-8.03 (m, 1H), 7.69 (d, 2H), 7.28 (d, 2H), 7.01-7.05 (m, 1H), 3.79 (s, 2H). EI-MS: m/z: 411.8 $[M+H]^+$.

After identification, the product obtained was indeed the target compound of Formula I-21.

Example 22. Synthesis of 2-(2-(2,5-difluoroanilino)acetylthio)nicotinate potassium (Formula I-22)

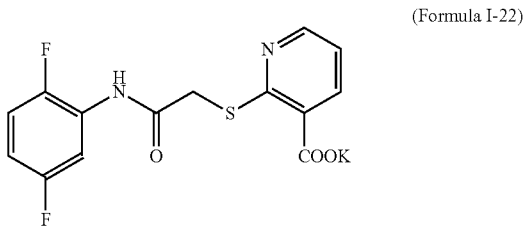
(Formula I-22)

With reference to the Example 3, 2-methoxy-5-chloroaniline was replaced with 2,5-difluoroaniline, with a yield of 78%.

Results of structural verification were as follows: 1H-NMR (DMSO-d6): 10.50 (s, 1H), 8.37 (d, 1H), 7.94-8.08 (m, 2H), 7.23-7.31 (m, 1H), 7.10-7.14 (m, 1H), 6.86-6.92 (m, 1H), 3.79 (s, 2H). EI-MS: m/z: 363.7 $[M+H]^+$.

After identification, the product obtained was indeed the target compound of Formula I-22.

Example 23. Synthesis of 2-(2-(5-chloro-2-benzyloxyanilino)acetylthio)nicotinate sodium (Formula I-23)

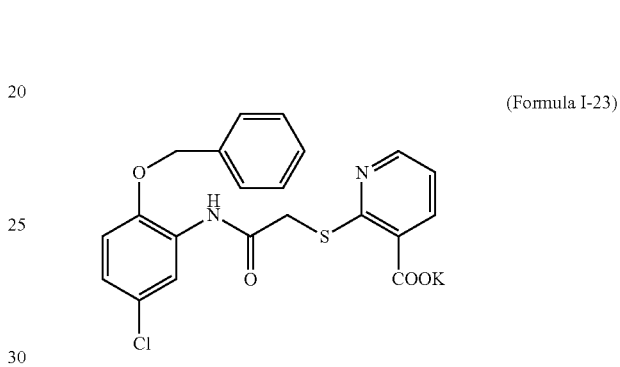
(Formula I-23)

3.47 g 2-nitro-4-chlorophenol, 3.76 g benzyl bromide, and 5.52 g anhydrous potassium carbonate were placed into 20 ml of DMF, and they were stirred at room temperature overnight, then the reaction solution was poured into 100 ml of iced water, large amount of light yellow solid was precipitated. After filtration, it was washed with water and dried to yield 2-benzyloxy-5-chloro-nitrobenzene. The described product was added to 40 mL of cold acetic acid, and 4.2 g of reduced iron powder was added. It was stirred at room temperature overnight, filtered, and washed, filtrates were combined, and placed into a 100 ml three-necked flask, after 2.5 g of chloroacetyl chloride was added in a dropwise manner, and it was stirred at room temperature overnight. The reaction solution was poured into 200 ml of iced water, and solid was precipitated, filtered, washed with water, and dried to yield the crude product for use directly in the next reaction.

Product from the previous step and 1.55 g 2-mercaptonicotinic acid were added into a mixed solution of 30 ml THF in water (volume ratio 1:1). After it was cooled to 0° C., 2.24 g of potassium hydroxide was added. The mixture was heated to room temperature, and stirred overnight. Large amount of solid was precipitated, filtered, washed with water, and dried to get 4.29 g off-white solid, with a yield of 92%.

Results of structural verification were as follows: 1H-NMR (DMSO-d6): 9.93 (s, 1H), 8.29 (d, 1H), 8.02-8.08 (m, 2H), 7.25-7.35 (m, 5H), 6.94-7.04 (m, 3H), 5.16 (s, 2H), 3.77 (s, 2H). EI-MS: m/z: 467.3 $[M+H]^+$.

After identification, the product obtained was indeed the target compound of Formula I-23.

Example 24. Synthesis of 2-(2-(2-trifluoromethoxyanilino)acetylthio)nicotinate potassium (Formula I-24)

(Formula I-24)

With reference to the Example 3, 2-methoxy-5-chloroaniline was replaced with 2-trifluoromethoxyaniline, with a yield of 75%.

Results of structural verification were as following:
1H-NMR (DMSO-d6): 9.98 (s, 1H), 8.32-8.35 (m, 1H), 8.05-8.14 (m, 2H), 7.31-7.36 (m, 2H, 7.08-7.19 (m, 2H), 3.79 (s, 2H). EI-MS: m/z: 411.5 [M+H]$^+$.

After identification, the product obtained was indeed the target compound of Formula I-24.

Example 25. Synthesis of 2-(2-(3-trifluoromethoxyanilino)acetylthio)nicotinate potassium (Formula I-25)

(Formula I-25)

With reference to the Example 3, 2-methoxy-5-chloroaniline was replaced with 3-trifluoromethoxyaniline, with a yield of 77%.

Results of structural verification were as following:
1H-NMR (DMSO-d6): 10.60 (s, 1H), 8.31-8.33 (m, 1H), 8.02-8.05 (m, 1H), 7.78 (s, 1H), 7.37-7.51 (m, 2H), 6.97-7.05 (m, 2H), 3.82 (s, 2H). EI-MS: m/z: 411.8 [M+H]$^+$.

After identification, the product obtained was indeed the target compound of Formula I-25.

Example 26. Synthesis of 2-(2-(5-trifluoromethoxy-2-bromoanilino)acetylthio)nicotinate potassium (Formula I-26)

(Formula I-26)

With reference to the Example 3, 2-methoxy-5-chloroaniline was replaced with 5-trifluoromethoxy-2-bromoaniline, with a yield of 81%.

Results of structural verification were as follows:
1H-NMR (DMSO-d6): 9.82 (s, 1H), 8.47-8.48 (m, 1H), 8.08-8.13 (m, 2H), 7.72 (d, 1H), 7.02-7.13 (m, 2H), 3.82 (s, 2H). EI-MS: m/z: 491.6 [M+H]$^+$.

After identification, the product obtained was indeed the target compound of Formula I-26.

Example 27. Synthesis of 2-(2-(5-fluoro-2-ethoxyanilino)acetylthio)nicotinic Acid (Formula I-27)

With reference to the Example 2 and 3, 2-methoxy-5-chloroaniline was replaced with 5-fluoro-2-ethoxyanilino, with a yield of 73%.

Results of structural verification were as following:
1H-NMR (DMSO-d6): 13.60 (s, 1H), 9.44 (s, 1H), 8.63-8.65 (m, 1H), 8.27-8.30 (m, 1H), 7.96-8.00 (m, 1H), 7.30-7.34 (m, 1H), 6.94-6.99 (m, 1H), 6.80-6.81 (m, 1H), 3.94-4.03 (m, 4H), 1.15 (t, 3H). EI-MS: m/z: 351.4 [M+H]$^+$.

After identification, the product obtained was indeed the target compound of Formula I-27.

Example 28. In Vitro Inhibition of Mercaptonicotinic Acid Compounds on Activity of Type A Botulinum Toxin Endopeptidase Activity of compounds was detected using FRET probes. Refer to Reference 5 (D. R. Ruge, F. M. Dunning, T. M. Piazza, B. E. Molles, M. Adler, F. N. Zeytin, W. C. Tucker, Detection of six serotypes of botulinum neurotoxin using fluorogenic reporters, J. Anal. Biochem. 2011, 411:200-209.) for the construction, expression purification of type A FRET probe. All FRET probes used in Examples of the present invention should be prepared according to the method described in this Reference. Refer to Reference 6 (L. Li, B. R. Singh, High-Level expression, purification, and characterization of recombinant type A botulinum neurotoxin light chain, Protein Expr Purif. 1999, 17:339-344.) for expression and purification of type A botulinum toxin light chain (BoNT/A-LC).

In 100 μl reaction solution (50 mM Hepes-NaOH pH 7.4, 10 mM NaCl, 0.1% Tween 20, 5 mM dithiothreitol, 10 μM $ZnCl_2$), simultaneously add BoNT/A-LC at a final concentration of 2 nM, FRET probe (for type A botulinum toxin) at a final concentration of 300 nM, and 10 μg compound (compound was dissolved in sterile water for test, or dissolved by using 2-5% DMSO if the compound cannot be dissolved in water), after mixing it was incubated at 37° C.

Dynamic fluorescence detection and analysis were completed with Synergy™ HT microplate reader (BioTek, USA), with a 96 holes FluoroNunc black plate purchased from Nunc of Denmark, and test conditions include an excitation wavelength of 420/50, emission wavelength of 485/20 and 528/20, respectively, at time interval of 2 min, and a detection period of 2 h. Data was analyzed and processed with software Prism 5.0 (Graphpad Software), 528/485 was plotted against time, the slope of the curve indicated the change of 528/485 per unit time, therefore, and the slope at any point on the curve was the reaction rate of the corresponding time. If the reaction rate was $V_0$ when no compound was added, the reaction rate was $V_i$ after compound was added, inhibition rate (percentage inhibition) i %=$(1-V_i/V_0)\times 100\%$.

Results of in vitro inhibitory activity of compounds detected by FRET probe were shown in Table 1, showing that each compound had different inhibition effect on activity of type A botulinum toxin endopeptidase, and the inhibition rate fall in the range of 2.7-78.0%, wherein the effect of inhibition in the Example 23 was significant, with an inhibition rate up to 78.0%, followed by Example 4, with an inhibition rate of 45.4%.

purification, and characterization of *Clostridium botulinum* type B light chain, Protein Expr Purif 46 (2006) 256-267.) for expression and purification of type B botulinum toxin light chain (BoNT/B-LC).

In 100 μl reaction solution (50 mM Hepes-NaOH pH 7.4, 10 mM NaCl, 0.1% Tween 20, 5 mM dithiothreitol, 10 μM $ZnCl_2$), simultaneously add BoNT/B-LC at a final concentration of 2 nM, FRET probe (for type B botulinum toxin) at a final concentration of 300 nM, and 10 μg compound. After mixing, it was incubated at 37° C. Dynamic fluorescence detection and analysis were completed with Synergy™ HT microplate reader (BioTek, USA), with a 96 holes FluoroNunc black plate purchased from Nunc of Denmark, and test conditions include an excitation wavelength of 420/50, emission wavelength of 485/20 and 528/20, respectively, at time interval of 2 min, and a detection period of 2 h. Data was analyzed and processed with software Prism 5.0 (Graphpad Software), 528/485 was plotted against time, the slope of the curve indicated the change of 528/485 per unit time, therefore, the slope at any point on the curve was the reaction rate of the corresponding time. If the reaction rate was $V_0$ when no compound was added, the reaction rate was

TABLE 1

Results of compound activity detected by FRET probe

Water soluble compounds

| No. | Example 4 | Example 1 | Example 3 | Example 8 | Example 9 | Example 10 | Example 11 | Example 12 | Example 14 |
|---|---|---|---|---|---|---|---|---|---|
| Inhibition rate % | 45.4 | 8.4 | 11.3 | 25.1 | 9.3 | 17.1 | 10.6 | 9.4 | 19.8 |

Water soluble compounds

| No. | Example 15 | Example 18 | Example 20 | Example 21 | Example 23 | Example 24 | Example 26 |
|---|---|---|---|---|---|---|---|
| Inhibition rate % | 3.0 | 11.4 | 6.8 | 14.3 | 78.0 | 8.9 | 27.4 |

Compounds solved in DMSO

| No. | Example 2 | Example 5 | Example 6 | Example 7 | Example 13 | Example 16 | Example 17 | Example 19 | Example 22 | Example 25 |
|---|---|---|---|---|---|---|---|---|---|---|
| Inhibition rate % | 12.1 | 2.7 | 14.7 | 18.1 | 20.3 | 17.9 | 15.4 | 3.0 | 3.2 | 2.9 |

Note:
Compound was dissolved in sterile water for test, or if the compound cannot be dissolved in water, it was dissolved by using 2-5% DMSO, test procedures were the same.

Example 29. In Vitro Inhibition of Mercaptonicotinic Acid Compounds on Activity of Type B Botulinum Toxin Endopeptidase Activity of compounds was detected using FRET probes. Refer to Reference 5 for the construction, expression purification of type B FRET probe. All FRET probes used in Examples of the present invention should be prepared according to the method described in this Reference; refer to Reference 7 (J. Gilsdorf, N. Gul, L. A. Smith, Expression, $V_i$ after compound was added, and the inhibition rate (percentage inhibition) i %=$(1-V_i/V_0)\times 100\%$.

Results of in vitro inhibitory activity of compounds in the present invention detected by FRET probe were shown in Table 2, showing that compounds of the present invention had different inhibition effect on activity of type B botulinum toxin endopeptidase, and the inhibition rate fall in the range of 2.7-95.5%, wherein, the effect of inhibition in the Example 4 was significant, with an inhibition rate up to 95.5%, followed by the compound in the Example 23, with an inhibition rate of 55.7%.

TABLE 2

Results of activity of compounds in the present invention detected by FRET probe Water soluble compounds

| No. | Example 4 | Example 1 | Example 3 | Example 8 | Example 9 | Example 10 | Example 11 | Example 12 | Example 14 |
|---|---|---|---|---|---|---|---|---|---|
| Inhibition rate % | 95.5 | 27.8 | 30.2 | 35.0 | 29.2 | 23.1 | 22.2 | 29.1 | 24.2 |

Water soluble compounds

| No. | Example 15 | Example 18 | Example 20 | Example 21 | Example 23 | Example 24 | Example 26 |
|---|---|---|---|---|---|---|---|
| Inhibition rate % | 19.4 | 30.2 | 41.0 | 28.0 | 55.7 | 29.3 | 30.0 |

Compounds solved in DMSO

| No. | Example 2 | Example 5 | Example 6 | Example 7 | Example 13 | Example 16 | Example 17 | Example 19 | Example 22 | Example 25 |
|---|---|---|---|---|---|---|---|---|---|---|
| Inhibition rate % | 20.5 | 4.3 | 8.6 | 24.2 | 22.0 | 20.1 | 3.7 | 3.0 | 2.7 | 15.2 |

Note:
Compound was dissolved in sterile water for test, or if the compound cannot be dissolved in water, it was dissolved using 2-5% DMSO, test procedures were the same.

Example 30. In Vitro Inhibition of Mercaptonicotinic Acid Compounds on Activity of Type E Botulinum Toxin Endopeptidase Activity of compounds was detected using FRET probes. Refer to Reference 5 for the construction, expression purification of type E FRET probe. All FRET probes used in Examples of the present invention should be prepared according to the method described in this Reference; refer to Reference 8 (Rakhi Agarwal, Subramaniam Eswaramoorthy, Desigan Kumaran, Cloning, high level expression, purification, and crystallization of the full length *Clostridium botulinum* neurotoxin type E light chain, Protein Expr Purif. 2004, 34:95-102) for expression and purification of type E botulinum toxin light chain (BoNT/E-LC).

In 100 µl reaction solution (50 mM Hepes-NaOH pH 7.4, 10 mM NaCl, 0.1% Tween 20, 5 mM dithiothreitol, 10 µM $ZnCl_2$), simultaneously add BoNT/E-LC at a final concentration of 2 nM, FRET probe (for type E botulinum toxin) at a final concentration of 300 nM, and 10 µg compound. After mixing, it was incubated at 37° C. Dynamic fluorescence detection and analysis were completed with Synergy™ HT microplate reader (BioTek, USA), with a 96 holes Fluoro-Nunc black plate purchased from Nunc of Denmark, and test conditions include an excitation wavelength of 420/50, emission wavelength of 485/20 and 528/20, respectively, at time interval of 2 min, and a detection period of 2 h. Data was analyzed and processed with software Prism 5.0 (Graphpad Software), 528/485 was plotted against time, the slope of the curve indicated the change of 528/485 per unit time, and the slope at any point on the curve was the reaction rate of the corresponding time. If the reaction rate was $V_0$ when no compound was added, the reaction rate was $V_i$ after compound was added, and the inhibition rate (percentage inhibition) i %=$(1-V_i/V_0) \times 100\%$.

Results of in vitro inhibitory activity of compounds detected by FRET probe were shown in Table 3, showing that compounds of the present invention had different inhibition effect on activity of type E botulinum toxin endopeptidase, and the inhibition rate fall in the range of 2.1-50.7%, wherein, the inhibition effect of Example 23 was significant, with an inhibition rate up to 50.7%, followed by Example 4, with an inhibition rate of 43.2%.

TABLE 3

Results of compound activity detected by FRET probe

Water soluble compounds

| No. | Example 4 | Example 1 | Example 3 | Example 8 | Example 9 | Example 10 | Example 11 | Example 12 | Example 14 |
|---|---|---|---|---|---|---|---|---|---|
| Inhibition rate % | 43.2 | 7.32 | 16.5 | 27.6 | 8.2 | 15.3 | 5.4 | 12.3 | 13.5 |

Water soluble compounds

| No. | Example 15 | Example 18 | Example 20 | Example 21 | Example 23 | Example 24 | Example 26 |
|---|---|---|---|---|---|---|---|
| Inhibition rate % | 16.3 | 17.2 | 4.2 | 20.3 | 50.7 | 5.6 | 12.1 |

TABLE 3-continued

Results of compound activity detected by FRET probe

Compounds solved in DMSO

| No. | Example 2 | Example 5 | Example 6 | Example 7 | Example 13 | Example 16 | Example 17 | Example 19 | Example 22 | Example 25 |
|---|---|---|---|---|---|---|---|---|---|---|
| Inhibition rate % | 11.6 | 6.8 | 16.8 | 14.0 | 18.3 | 5.2 | 18.0 | 6.8 | 2.1 | 4.3 |

Note:
Compound was dissolved in sterile water for test, or if the compound cannot be dissolved in water, it was dissolved using 2-5% DMSO, test procedures were the same.

Example 31. In Vitro Inhibition of Mercaptonicotinic Acid Compounds on Activity of Type F Botulinum Toxin Endopeptidase Activity of compounds was detected using FRET probes. Refer to Reference 5 for the construction, expression purification of type F FRET probe, and all FRET probes used in Examples of the present invention should be prepared according to the method described in this Reference; refer to Reference 9 (Yang K. H., Sugiyama H. Purification and Properties of *Clostridium botulinum* Type F Toxin, Appl. Microbiol. 1975, 29(5):598-603) for purification of type F botulinum toxin (BoNT/F).

In 100 μl reaction solution (50 mM Hepes-NaOH pH 7.4, 10 mM NaCl, 0.1% Tween 20, 5 mM dithiothreitol, 100 μ ZnCl$_2$), simultaneously add BoNT/F-LC at a final concentration of 2 nM, FRET probe (for type F botulinum toxin) at a final concentration of 300 nM, and 10 μg compound. After mixing, it was incubated at 37° C. Dynamic fluorescence detection and analysis were completed with Synergy™ HT microplate reader (BioTek, USA), with a 96 holes Fluoro-Nunc black plate purchased from Nunc of Denmark, and test conditions include an excitation wavelength of 420/50, emission wavelength of 485/20 and 528/20, respectively, at time interval of 2 min, and a detection period of 2 h. Data was analyzed and processed with software Prism 5.0 (Graphpad Software), 528/485 was plotted against time, the slope of the curve indicating the change of 528/485 per unit time, and thus the slope at any point on the curve was the reaction rate of the corresponding time. If the reaction rate was $V_0$ when no compound was added, the reaction rate was $V_i$ after compound was added, and the inhibition rate (percent inhibition) i %=$(1-V_i/V_0) \times 100\%$.

Results of in vitro inhibitory activity of compounds detected by FRET probe were shown in Table 4, showing that compounds of the present invention had different inhibition effect on activity of type F botulinum toxin endopeptidase, and the inhibition rate fall in the range of 3.0-48.6%, wherein, the inhibition effect of the Example 4 was significant, with an inhibition rate up to 48.6%, followed by the Example 23, with an inhibition rate of 35.8%.

TABLE 4

Results of compound activity detected by FRET probe

Water soluble compounds

| No. | Example 4 | Example 1 | Example 3 | Example 8 | Example 9 | Example 10 | Example 11 | Example 12 | Example 14 |
|---|---|---|---|---|---|---|---|---|---|
| Inhibition rate % | 48.6 | 12.2 | 19.2 | 15.3 | 12.1 | 16.5 | 6.4 | 13.2 | 9.8 |

Water soluble compounds

| No. | Example 15 | Example 18 | Example 20 | Example 21 | Example 23 | Example 24 | Example 26 |
|---|---|---|---|---|---|---|---|
| Inhibition rate % | 7.2 | 16.2 | 17.8 | 16.5 | 35.8 | 11.2 | 13.1 |

Compounds solved in DMSO

| No. | Example 2 | Example 5 | Example 6 | Example 7 | Example 13 | Example 16 | Example 17 | Example 19 | Example 22 | Example 25 |
|---|---|---|---|---|---|---|---|---|---|---|
| Inhibition rate % | 13.2 | 5.0 | 6.7 | 11.3 | 16.4 | 9.8 | 8.3 | 4.0 | 3.4 | 3.0 |

Note:
Compound was dissolved in sterile water for test, or if the compound cannot be dissolved in water, it was dissolved using 2-5% DMSO, test procedures were the same.

Example 32. In Vitro Inhibition of Mercaptonicotinic Acid Compounds on Activity of Tetanus Toxin Endopeptidase Activity of compounds was detected using FRET probes. Refer to Reference 5 for the construction, expression purification of tetanus toxin FRET probe, and all FRET probes used in Examples of the present invention should be prepared following the method described in this Reference Refer to Reference 10 (Fiorella Tonello, Rossella Pellizzari, Sebastiano Pasqualato, Recombinant and Truncated Tetanus Neurotoxin Light Chain: Cloning, Expression, Purification, and Proteolytic Activity, Protein Expr Purif. 1999, 15:221-227) for expression and purification of tetanus toxin light chain (TeNt-LC).

In 100 μl reaction solution (50 mM Hepes-NaOH pH 7.4, 10 mM NaCl, 0.1% Tween 20, 5 mM dithiothreitol, 10 μM $ZnCl_2$), simultaneously add TET-LC at a final concentration of 2 nM, FRET probe (for tetanus toxin) at a final concentration of 300 nM, and 20 μg compound. After mixing, it was incubated at 37° C. Dynamic fluorescence detection and analysis were completed with Synergy™ HT microplate reader (BioTek, USA), with a 96 holes FluoroNunc black plate purchased from Nunc of Denmark, and test conditions include an excitation wavelength of 420/50, emission wavelength of 485/20 and 528/20, respectively, at time interval of 2 min, and a detection period of 2 h. Data was analyzed and processed with software Prism 5.0 (Graphpad Software), 528/485 was plotted against time, the slope of the curve indicating the change of 528/485 per unit time, and thus the slope at any point on the curve was the reaction rate of the corresponding time. If the reaction rate was $V_0$ when no compound was added, the reaction rate was $V_i$ after compound was added, and the inhibition rate (percent inhibition) i %=$(1-V_i/V_0) \times 100\%$.

Results of in vitro inhibitory activity of compounds detected by FRET probe were shown in Table 5, showing that compounds of the present invention had different inhibition effect on activity of tetanus toxin endopeptidase, and the inhibition rate fall in the range of 2.7-34.5%, wherein, the inhibition effect of the Example 4 was significant, with an inhibition rate up to 34.5%, followed by the Example 23, with an inhibition rate of 30.3%.

extraction and identification of type A botulinum toxin (BoNT/A), and Balb/c mices of 14-16 g were purchased from Military Academy of Medical Sciences Laboratory Animal Center.

Refer to Reference 12 (C. H. Hatheway, J. D. Snyder, J. E. Seals, T. A. Edell, G. E. Lewis, Jr. Antitoxin levels in botulism patients treated with trivalent equine botulism antitoxin to toxin types A, B, and E. Infect Dis 1984, 150: 145-151.) for experiment on protection against botulinum toxin poisoning.

Description of the model of botulism to the mice was summarized as follows: taking the Balb/C mice as experiment animals, which were randomized into groups, with 10 mice/group. Type A antitoxin horse serum was used as positive control, 200 μg of different compounds as samples were tested (partial water-soluble compounds with inhibition on enzyme activity, see Table 6), respectively, mixing with type A botulinum toxin at 5 times of half lethal dose 50 ($5LD_{50}$), incubated at 37° C. for 30 min, 500 μl/animal, intraperitoneal injection, meanwhile a placebo group was established. Mice were observed continually for more than five days, to observe the sign of botulism (such as occurrence of wasp waist, horripilation, weak breathing, limb paralysis until death), and survival time of mice was recorded, calculate survival rates.

The model of anti-poisoning effect of compounds against botulism to the mice was shown in Table 6, showing the compounds of the present invention can suppress the lethal

TABLE 5

Results of compound activity detected by FRET probe

Water soluble compounds

| No. | Example 4 | Example 1 | Example 3 | Example 8 | Example 9 | Example 10 | Example 11 | Example 12 | Example 14 |
|---|---|---|---|---|---|---|---|---|---|
| Inhibition rate % | 34.5 | 12.8 | 20.2 | 21.1 | 15.2 | 18.6 | 11.3 | 16.4 | 12.3 |

Water soluble compounds

| No. | Example 15 | Example 18 | Example 20 | Example 21 | Example 23 | Example 24 | Example 26 |
|---|---|---|---|---|---|---|---|
| Inhibition rate % | 23.5 | 19.3 | 22.2 | 17.4 | 30.3 | 13.2 | 17.1 |

Compounds solved in DMSO

| No. | Example 2 | Example 5 | Example 6 | Example 7 | Example 13 | Example 16 | Example 17 | Example 19 | Example 22 | Example 25 |
|---|---|---|---|---|---|---|---|---|---|---|
| Inhibition rate % | 12.3 | 8.0 | 4.7 | 20.0 | 14.6 | 16.2 | 6.4 | 2.7 | 4.4 | 5.7 |

Note:
Compound was dissolved in sterile water for test, or if the compound cannot be dissolved in water, it was dissolved using 2-5% DMSO, test procedures were the same.

Example 33. Protection Effect of Mercaptonicotinic Acid Compounds Against Type A Botulinum Toxin Poisoning in Animal Refer to Reference 11 (C. J. Malizio, M. C. Goodnough, E A Johnson, Purification of *Clostridium botulinum* type A neurotoxin, Methods Mol Biol. 2000, 145:27-39.) for effects of type A botulinum toxin at different extent in the testing animals, wherein compounds in the Example 4 and 23 had the highest protection rate (100%), followed by the Example 8, the Example 15, the Example 10, the Example 3, the Example 21, the Example 14, in which protection rates were 80%, 80%, 60%, 40%, 40%, and 20% in descending order.

TABLE 6

Anti-poisoning effect of compounds of the present invention in the model of botulism to the mice

| Group | Placebo | Type A horse serum antitoxin | Example 4 | Example 3 | Example 8 | Example 10 | Example 14 | Example 15 | Example 18 | Example 21 | Example 23 |
|---|---|---|---|---|---|---|---|---|---|---|---|
| % survival | 0 | 100 | 100 | 40 | 80 | 60 | 20 | 80 | 0 | 40 | 100 |

Note:
The placebo agent was normal saline in Table 6. Antitoxin was type A antitoxin horse serum (purchased from National Institutes for Food and Drug Control).

Example 34. Protection Effect of Mercaptonicotinic Acid Compounds Against Type B Botulinum Toxin Poisoning in Animal Refer to Reference 13 (H. Arimitsu, K. Inoue, Y. Sakaguchi, J. Lee, Y. Fujinaga, T. Watanabe, T. Ohyama, R. Hirst, K. Oguma, Purification of fully activated *Clostridium botulinum* serotype B toxin for treatment of patients with dystonia, Infect Immun. 71(2003)1599-1603.) for extraction and identification of type B botulinum toxin (BoNT/B), and Balb/c mice of 14-16 g were purchased from Military Academy of Medical Sciences Laboratory Animal Center.

Protection experiment of botulinum toxin poisoning refers to the model of botulism on mice as described in Reference 12, the method was summarized as following: taking the Balb/C mice as experiment animals, which were randomized into groups, with 10 mice/group. Type B horse serum antitoxin was used as positive control, 200 μg of different compounds as samples were tested (partial water-soluble compounds with inhibition on enzyme activity), respectively, mixing with type B botulinum toxin at 5 times of half lethal dose 50 ($5LD_{50}$), incubated at 37° C. for 30 min, 500 μl/animal, intraperitoneal injection, meanwhile a placebo group was established. Mice were observed continually for more than five days, to observe the sign of botulism (such as occurrence of wasp waist, horripilation, weak breathing, limb paralysis until death), and survival time of mice was recorded, calculate survival rates.

The model of anti-poisoning effect of compounds against botulism to the mice was shown in Table 7, compounds of the present invention can suppress the lethal effects of type B botulinum toxin at different extent in the testing animals, wherein compound in the Example 4 had the highest protection rate (100%), followed by the high protecting efficiency of compounds in the Example 23, Example 24 and Example 12 (80%), additionally compounds in the Example 1, Example 3, Example 9, Example 18, Example 21, Example 26, in which protection rates were 40%, 60%, 20%, 40%, 40%, and 20%, respectively.

INDUSTRIAL APPLICABILITY

The present invention provides a class of mercaptonicotinic acid compounds and preparation method and use thereof, and these substances have inhibiting activity to botulinum toxin endopeptidase or tetanus toxin endopeptidase, so as to use as an active ingredient of inhibitory medicine of botulinum toxin endopeptidase or *Clostridium* tetanus toxin endopeptidase or medicine against botulism or tetanus, and be used in the development of medicine for prevention and treatment of botulism or tetanus disease and related medicines.

The invention claimed is:

1. A mercaptonicotinic acid compound, a pharmaceutically acceptable salt, ester, or solvate thereof, wherein, the compound is selected from:

(Formula I-1)

(Formula I-2)

TABLE 7

Anti-poisoning effect of compounds of the present invention in the model of botulism to the mice

| Compounds | Placebo | Antitoxin | Example 4 | Example 1 | Example 3 | Example 8 | Example 9 | Example 10 | Example 12 | Example 18 | Example 20 | Example 21 | Example 23 | Example 24 | Example 26 |
|---|---|---|---|---|---|---|---|---|---|---|---|---|---|---|---|
| % survival | 0 | 100 | 100 | 40 | 60 | 0 | 20 | 0 | 80 | 40 | 0 | 40 | 80 | 80 | 20 |

Note:
The placebo agent was normal saline in Table 7. Antitoxin was type B antitoxin serum (purchased from National Institutes for Food and Drug Control).

-continued (Formula I-3)

(Formula I-4)

(Formula I-5)

(Formula I-6)

(Formula I-7)

(Formula I-8)

(Formula I-10)

(Formula I-12)

(Formula I-13)

(Formula I-14)

(Formula I-15)

(Formul I-17)

(Formula I-18)

(Formula I-19)

(Formula I-20)

-continued (Formula I-21)

(Formula I-23)

(Formula I-24)

(Formula I-25)

(Formula I-26)

(Formula I-27)

2. A mercaptonicotinic acid compound, a pharmaceutically acceptable salt, ester, or solvate thereof according to claim 1, wherein, the pharmaceutically acceptable salt is an inorganic or organic salt.

3. A mercaptonicotinic acid compound, pharmaceutically acceptable salt, ester, or solvate thereof according to claim 2, wherein, the inorganic salt is selected from the group consisting of hydrochloride, sulfate, phosphate, diphosphate, hydrogen phosphate, hydrobromide or nitrate, and the organic salt is selected from the group consisting of acetate, maleate, fumarate, tartrate, succinate, lactate, citrate, p-toluenesulfonate, salicylate, oxalate, palmitate or stearate.

4. A mercaptonicotinic acid compound, pharmaceutically acceptable salt, esters or solvate thereof according to claim 1, wherein, the pharmaceutically acceptable ester refers to a C1-C6 alkyl ester.

5. A mercaptonicotinic acid compound, pharmaceutically acceptable salt, ester, or solvate thereof according to claim 1, wherein, the pharmaceutically acceptable solvate refers to solvated form formed with water, alcohol or DMSO.

6. A composition comprising an active ingredient selected from a mercaptonicotinic acid compound, a pharmaceutically acceptable salt, or solvate thereof according to claim 1.

7. A composition according to claim 6, wherein, said composition is an inhibitor of botulinum toxin endopeptidase, an inhibitor of tetanus toxin endopeptidase, a medicament for treating botulinum toxin poisoning, or a medicament for treating tetanus.

8. A composition according to claim 6, wherein said composition is an inhibitor of botulinum toxin endopeptidase, a medicament for treating botulinum toxin poisoning, wherein the active ingredient includes one following compound or a mixture comprising more of the compounds following:
 a) 2-(2-(3-chloro-5-methoxyanilino)acetylthio)nicotinic acid;
 b) 2-(2-(3-chloro-5-methoxyanilino)acetylthio)nicotinate sodium;
 c) pharmaceutically acceptable salts, esters, or solvates of a) or b);
 d) 2-(2-(5-chloro-2-benzyloxyanilino)acetylthio)nicotinic acid;
 f) 2-(2-(5-chloro-2-benzyloxyanilino)acetylthio)nicotinate sodium; and
 g) pharmaceutically acceptable salts, esters, or solvates of d) or f).

9. A composition according to claim 6, wherein said composition is an inhibitor of tetanus toxin endopeptidase or a medicament for treating tetanus, wherein an active ingredient includes one following compound or a mixture comprising more of the compounds following:
 a) 2-(2-(3-chloro-5-methoxyanilino)acetylthio)nicotinic acid;
 b) 2-(2-(3-chloro-5-methoxyanilino)acetylthio)nicotinate sodium;
 c) pharmaceutically acceptable salts, esters, or solvates of a) or b);
 d) 2-(2-(5-chloro-2-benzyloxyanilino)acetylthio)nicotinic acid;
 f) 2-(2-(5-chloro-2-benzyloxyanilino)acetylthio)nicotinate sodium; and
 g) pharmaceutically acceptable salts, esters, or solvates of d) or f).

* * * * *

UNITED STATES PATENT AND TRADEMARK OFFICE
CERTIFICATE OF CORRECTION

PATENT NO. : 10,035,771 B2
APPLICATION NO. : 14/892219
DATED : July 31, 2018
INVENTOR(S) : Wang et al.

Page 1 of 1

It is certified that error appears in the above-identified patent and that said Letters Patent is hereby corrected as shown below:

In the Assignee (73):
Delete "INSTITUTE OF MICROBIOLOGY AND EPIDEMIOLOGY, ACADEMY OF MILITARY MEDICAL SCIENCES, PR CHINA, Beijing (CN)"
And insert -- INSTITUTE OF MICROBIOLOGY AND EPIDEMIOLOGY, ACADEMY OF MILITARY MEDICAL SCIENCES, PR CHINA, Beijing (CN); and THE SECOND MILITARY MEDICAL UNIVERSITY, Shanghai, (CN) --

Signed and Sealed this
Second Day of October, 2018

Andrei Iancu
*Director of the United States Patent and Trademark Office*